United States Patent [19]
Mayhew et al.

[11] Patent Number: 5,762,958
[45] Date of Patent: Jun. 9, 1998

[54] MULTILIPID COMPONENT ETHER LIPID LIPOSOMES

[75] Inventors: Eric Mayhew, Monmouth Junction, N.J.; Andrew S. Janoff, Yardley, Pa.; Imran Ahmad, Cranbury, N.J.; Suresh K. Bhatia, New Delhi, India

[73] Assignee: The Liposome Company, Inc., Princeton, N.J.

[21] Appl. No.: 602,669

[22] Filed: Feb. 16, 1996

Related U.S. Application Data

[63] Continuation-in-part of Ser. No. 323,042, Oct. 14, 1994, abandoned.

[51] Int. Cl.$^6$ .................................................. A61K 9/127
[52] U.S. Cl. ........................................ 424/450; 428/402.2
[58] Field of Search ............................ 424/450, 1.21, 424/9.321, 9.51; 428/402.2

[56] References Cited

U.S. PATENT DOCUMENTS

| | | | |
|---|---|---|---|
| 3,752,886 | 8/1973 | Munder et al. | 424/199 |
| 4,159,988 | 7/1979 | Eibl et al. | 260/340.9 |
| 4,163,748 | 8/1979 | Eibl et al. | 260/403 |
| 4,382,035 | 5/1983 | Eibl | 260/403 |
| 4,734,225 | 3/1988 | Eibl | 260/386 |
| 4,804,789 | 2/1989 | Eibl | 568/853 |
| 4,920,016 | 4/1990 | Allen et al. | 424/450 |
| 4,965,391 | 10/1990 | Counsell et al. | 558/169 |
| 4,983,397 | 1/1991 | Schroit | 424/450 |
| 5,013,556 | 5/1991 | Woodle et al. | 424/450 |
| 5,436,234 | 7/1995 | Eibl | 514/77 |

FOREIGN PATENT DOCUMENTS

| | | | |
|---|---|---|---|
| 4132345 | 4/1993 | Germany . | |
| 4408011 | 11/1995 | Germany | A61K 31/685 |
| 072294 | 7/1984 | Japan . | |
| 1583661 | 1/1981 | United Kingdom | A61K 31/66 |
| 93/04673 | 3/1993 | WIPO | A61K 9/127 |
| 93/08202 | 4/1993 | WIPO | C07H 15/04 |
| 94/27580 | 12/1994 | WIPO | A61K 9/127 |

OTHER PUBLICATIONS

Mende, CA 110(23): 205219g.
Baker Int. J. Immunopharm 13, #4, p. 385, 1991.
Kucera AIDS Res. & Human Retroviruses 6 #4 p. 491 1990.
Bazill, et al., "Role of Endocytosis in the Action of Ether Lipids on WEHI–3B, HL60 and FEDCP–Mix A4 Cells", Cancer Res. 50: 7505 (1990).
Berdel, "Membrane–interactive lipids as experimental anticancer drugs", Br. J. Cancer 64: 208 (1991).
Berdel, "Ether Lipids and Derivatives as Investigational Anticancer Drugs", Onkologie 13: 245 (1990).
Bhatia, et al., "Sterospecific Systhesis of Antitumor Active Thioether PAF Analogs", Lipids 26(12): 1424 (1991).
Blume et al, "Specific targeting with poly(ethylene glycol)–modified liposomes: coupling of homing devices to the ends of the polymeric chains combines effective target binding with long circulation times" Biochim. Biophys. Acta. 1149: 180–184 (1993).

(List continued on next page.)

*Primary Examiner*—Gollamudi S. Kishore
*Attorney, Agent, or Firm*—Kenneth B. Rubin

[57] ABSTRACT

Liposomes are provided which contain ether lipids having the formula:

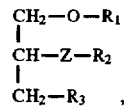

as well as an underivatized phosphatidylethanolamine, a sterol, and a phosphatidylethanolamine-dicarboxylic acid headgroup-derivatized lipid. These liposomes are useful in a variety of therapeutic regimens, including the treatment of cancers and inflammatory disorders.

20 Claims, 3 Drawing Sheets

OTHER PUBLICATIONS

Daicho, et al., "Effects of alkyl glycosides incorporated into liposomes prepared from synthetic amphiphiles on their tissue distribution in Ehrlich solid tumor–bearing mice", BBA, 1107:61 (1992).

Darnell et al., *Molecular Cell Biology*, Scientific American Books, Inc. (1986), New York, pp. 573–575.

Deamer and Uster, "Liposome Preparation: Methods and Mechanisms," in: *Liposomes* (M. Ostro, ed.), Marcel Dekker, Inc., New York (1983), pp. 27–52.

Dietzfelbinger et al., "Removal of Breast Cancer Cells from Bone Marrow by in Vitro Purging with Ether Lipids and Cryopreservation", Cancer Res. 53: 3747 (1993).

Dive, et al., "Multiparametric Flow Cytometry of the Modulation of Tumore Cell Membrane Permeability by Developmental Antitumore Ether Lipid SRI 62–834 in EMT6 Mouse Mammary Tumor and HL–60 Human Promyelocytic Leukemia Cells", Cancer Res., 51:799 (1991).

Gabizon et al., "Prolongation of Circulation Time of Doxorubicin Encapsulated in Liposomes Containing a Polyethylene Glycol–Derivatized Phospholipid: Pharmacokinetic Studies in Rodents and Dogs", Pharm. Res. 10(5): 703 (1993).

Kaufmann–Kolle, et al., "Liposomal Hexadecylphosphocholine (HEPC): in Vitro and in Vivo Application", Chemical Abs. V4, 10.08.

Layton et al., "The Interaction of Liposomes with Cells: The Relation of Cell Specific Toxicity to Lipid Composition", Eur. J. Cancer 16: 64 (1980).

Lewis and McElhaney, "The Mesomorphic Phase Behavior of Lipid Bilayers," in *The Structure of Biological Membranes* (P. Yeagle, ed.), CRC Press, Inc. (1992), Boca Raton, Fl., pp. 73–155, at pp. 123–126.

Muschiol et al., "Alkyl Phosphocholine: Toxicity and Anticancer Properties", Lipids 22(11): 930 (1987).

Nairn, in: *Remington's Pharmaceutical Science* (A. Gennaro, ed).. Mack Publishing Co., Easton, PA, (1985), pp. 1492–1517.

Park et al., "Some negatively charged phospholipid derivatives prolong the liposome circulation in vivo", Biochim. Biophys. Acta. 1108: 257 (1992).

Powis et al., "Selective Inhibition of Phophatidylinositol Phospholipase C by Cytotoxic Ether Lipid Analogues", Cancer Res. 52: 2835 (1992).

Powis et al., "The Cell Membrane and Cell Signals as Targets in Cancer Chemotherapy", Cancer Res. 50: 2203 (1990).

Reed et al., "Antineoplastic Ether–linked Phopholipid induces differentiation of acute myelogenous leukemic KG–1 cells into marcophase–like cells", Life Sci. 49: 1221 (1991).

Runge et al., "Destruction of Human Solid Tumors by Alkyl Lysophopholipids", JNCI. 64(6): 1301 (1980).

Tritton, et al., "How to Kill Cancer Cells: Membranes and Cell Signaling as Targets in Cancer Chemotherapy", Cancer Cells 2(4): 95 (1990).

Workman, "Antitumor Ether Lipids: Endocytosis as a Determinant of Cellular Sensitivity", Cancer Cells 3(8): 315 (1991).

Workman et al., "Plastelet–activating factor (PAF) antagonist WEB 2086 does not modulate the cytotoxicity of PAF or antitumour alkyl lysophospholipids ET–18–O–Methyl and SRIU 62–834 in HL–60 promyelocytic leukaemia cells", Biochem. Pharmacol. 41(2): 319 (1991).

Zeisig et al., "Antineoplastic activity in vitro of free and liposomal alkylphophocholines", Anti–Cancer Drugs 4: 57 (1993).

MULTILIPID COMPONENT ETHER LIPID LIPOSOMES

This application is a CIP of U.S. Ser. No. 08/323,042 filed Oct. 14, 1994 ABN.

Ether lipids are synthetic analogues of platelet activating factor (PAF; 1-O-alkyl-2-acetyl-sn-glycero-3-phosphocholine), an effector generally believed to be involved in a variety of physiological processes, such as inflammation, the immune response, allergic reactions and reproduction. Ether lipids have been shown to be effective antitumor agents in animals, and are believed to be selectively cytotoxic to a broad variety of cancer cells (see, for example, Dietzfelbinger et al. (1993); Zeisig et al. (1993); Powis et al. (1990); Berdel (1991); Bhatia and Hadju (1991); Reed et al. (1991); Workman (1991); Workman et al. (1991); Bazill and Dexter (1990); Berdel (1990); Counsell et al. (1990); Tritton and Hickman (1990); Muschiol et al. (1990); Layton et al. (1980); Runge et al. (1980); Great Britain Patent No. 1,583,661; U.S. Pat. No. 3,752,886). Ether lipids have also been shown to be antimetastatic and anti-invasive, and to be capable of cell differentiation induction.

Mechanisms of ether lipid cytotoxicity, while not definitively established, appear to involve action at, and possible disruption of, the cell membrane. The selective cytotoxicity of ether lipids may involve intracellular accumulation and differential activity of alkyl cleavage enzymes. Ether lipids may also be selective inhibitors of phosphatidylinositol phospholipase C and protein kinase C activities, as well as of phosphatidylcholine biosynthesis. Ether lipids are, because of their antitumor activity, potentially useful therapeutically. However, their administration can also lead to hemolysis, hepatic dysfunction and gastrointestinal disorders. Applicants have found that certain liposomal formulations of ether lipids can buffer these toxicities without inhibiting anticancer efficacy, and thereby can provide a more therapeutically useful basis for ether lipid administration.

SUMMARY OF THE INVENTION

This invention provides a liposome having a lipid bilayer which comprises: (a) an underivatized phosphatidylethanolamine; (b) a sterol; (c) a headgroup derivatized lipid containing a phosphatidylethanolamine and a dicarboxylic acid, which derivatized lipid comprises from about 5 mole percent to about 20 mole percent of the bilayer; and, (d) an ether lipid having the following formula:

the ether lipid comprising from greater than about 10 mole percent, to less than about 30 mole percent, of the bilayer. $R_1$ is $Y_1Y_2$, $Y_2$ is $CH_3$ or $CO_2H$, $Y_1$ is $(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}$, the sum of n1+2n2+n3+2n4+n5+2n6+n7+2n8+n9 is an integer of from 3 to 23, n1 is zero or an integer of from 1 to 22, n3 is zero or an integer of from 1 to 19, n5 is zero or an integer of from 1 to 16, n7 is zero or an integer of from zero to 13, n9 is zero or an integer of from 1 to 10, and each of n2, n4, n6 and 8 is independently zero or 1.

Z is oxygen, sulfur, NH, or —NHC(O)—, Z then being connected to the methyl group by way of either the nitrogen or carbonyl carbon. Z can also be —OC(O)—, it then being connected to the methyl group by way of either the oxygen or carbonyl carbon atom. Preferably, Z is O; accordingly, this invention's glycerol-based ether lipids preferably have a methoxy group at the sn-2 position of their glycerol backbone.

$R_2$ is an alkyl group, or a halogen-substituted alkyl group, having the formula $(C(X_1)_{n10}(X_2)_{n11})_{n12}CX_3X_4X_5$, wherein each of $X_1$, $X_2$, $X_3$, $X_4$, and $X_5$ is independently hydrogen or a halogen, but is preferably hydrogen. n10 is equal to zero, 1 or 2; n11 is equal to zero, 1, or 2; and n12 is equal to zero or an integer of from 1 to 23, but is most preferably, zero. $R_2$ then being $CX_3X_4X_5$. $X_3$, $X_4$, and $X_5$ are most preferably H, and $R_2$ then being $CH_3$. However, $R_2$ can then also be $CH_2F$, $CHF_2$ or $CF_3$. When n12 is not zero, the sum of n10+n11 is equal to 2, n12 is preferably equal to 1, and $R_2$ is preferably $CH_2CH_3$, $CH_2CF_3$ or $CF_2CF_3$.

Preferably, the ether lipid is one in which $Y_2$ is $CH_3$, $R_1$ is $(CH_2)_{n1}CH_3$, R2 is $CH_3$ and Z is O. Most preferably, the ether lipid is also known as "ET-18-OCH$_3$," or "edelfosine").

Preferably, the liposome is a unilamellar liposome having a diameter of from greater than about 50 nm to less than about 200 nm, the underivatized phosphatidylethanolamine is an unsaturated or partially unsaturated phosphatidylethanolamine, more preferably, dioleoyl phosphatidylethanolamine, and the sterol is cholesterol. The headgroup derivatized lipid preferably comprises a phosphatidylethanolamine ("PE") selected from the group consisting of dipalmitoyl phosphatidylethanolamine, palmitoyloleoyl phosphatidylethanolamine and dioleoyl phosphatidylethanolamine, and a dicarboxylic acid selected from the group consisting of glutaric acid, sebacic acid, succinic acid and tartaric acid. More preferably, the PE is dioleoyl phosphatidylethanolamine and the dicarboxylic acid is glutaric acid. Still more preferably, the headgroup-derivatized lipid comprises dioleoyl phosphatidylethanolamine and glutaric acid.

Preferred embodiments of this invention's liposome have bilayers containing dioleoyl phosphatidylethanolamine as the underivatized PE, cholesterol as the sterol, dioleoyl phosphatidylethanolamine-glutaric acid as the headgroup-derivatized lipid and ET-18-OCH$_3$ as the ether lipid. Most preferably, presently, the liposome's bilayer comprises about 20 mole percent of the ether lipid, about 10 mole percent of the headgroup-derivatized lipid, about 30 mole percent cholesterol and about 40 mole percent dioleoyl phosphatidylethanolamine. The liposome can further comprise an additional bioactive agent, that is an agent in addition to the ether lipid.

Also provided herein is a pharmaceutical composition comprising a pharmaceutically acceptable carrier and the liposomes of this invention. Further provided is a method of treating a mammal afflicted with a cancer, including, but not limited to: a lung, brain, colon, ovarian or breast cancer. The method comprises administering the compositions of this invention to the mammal, in an amount containing an anticancer effective amount of the ether lipid. Preferably, the liposome administered is a unilamellar liposome having an average diameter of from about 50 nm to about 200 nm. Typically, the anticancer effective amount of the ether lipid is from about 0.1 mg of the ether lipid per kg of the body weight of the mammal to about 1000 mg per kg.

The method can also comprise administration of an additional bioactive agent, e.g., an antineoplastic agent, antimicrobial agent, therapeutic lipid or hematopoietic cell growth stimulating agent, to the mammal. Administration of such an additional agent is typically of an effective amount of the additional agent in connection with an anticancer effective amount of the ether lipid. However, when the additional agent is an anticancer agent, either the additional agent, the ether lipid, or both can be administererd in a "sub-anticancer effective amount," that is, in an amount which may not be effective against a cancer on its own.

Still further provided herein is a method of treating a mammal afflicted with an inflammatory disorder, e.g., an arthritic condition, asthmatic disorder or allergic reaction, which comprises administering this invention's pharmaceutical composition to the mammal, in an amount containing an anti-inflammation effective amount of the ether lipid. Typically, the anti-inflammation effective amount of the ether lipid is from about 0.1 mg of the ether lipid per kg of the body weight of the mammal to about 1000 mg per kg. Additional bioactive agents, such as additional anti-inflammatory agents, can also be administered when the liposomes of this invention are used against inflammatory disorders.

DETAILED DESCRIPTION OF THE INVENTION

This invention provides a liposome having a lipid bilayer which comprises: (a) an underivatized phosphatidylethanolamine; (b) a sterol; (c) a headgroup derivatized lipid containing a phosphatidylethanolamine and a dicarboxylic acid, which derivatized lipid comprises from about 5 mole percent to about 20 mole percent of the bilayer; and, (d) an ether lipid having the following formula:

the ether lipid comprising from greater than about 10 mole percent, to less than about 30 mole percent, of the bilayer.

"Liposomes" are self-assembling structures comprising one or more lipid bilayers, each of which surrounds an aqueous compartment and comprises two opposing monolayers of amphipathic lipid molecules. Amphipathic lipids comprise a polar (hydrophilic) headgroup region covalently linked to one or two non-polar (hydrophobic) acyl chains. Energetically unfavorable contacts between the hydrophobic acyl chains and the aqueous medium are generally believed to induce lipid molecules to rearrange such that the polar headgroups are oriented towards the aqueous medium while the acyl chains reorient towards the interior of the bilayer. An energetically stable structure is formed in which the acyl chains are effectively shielded from coming into contact with the aqueous medium.

Liposomes can have a single lipid bilayer (unilamellar liposomes, "ULVs"), or multiple lipid bilayers (multilamellar liposomes, "MLVs"), and can be made by a variety of methods (for a review, see, for example, Deamer and Uster (1983)). These methods include without limitation: Bangham's methods for making multilamellar liposomes (MLVs); Lenk's, Fountain's and Cullis' methods for making MLVs with substantially equal interlamellar solute distribution (see, for example, U.S. Pat. Nos. 4,522,803, 4,588,578, 5,030,453, 5,169,637 and 4,975,282); and Paphadjopoulos et al.'s reverse-phase evaporation method (U.S. Pat. No. 4,235,871) for preparing oligolamellar liposomes. ULVs can be produced from MLVs by such methods as sonication (see Paphadjopoulos et al. (1968)) or extrusion (U.S. Pat. No. 5,008,050 and U.S. Pat. No. 5,059,421). The ether lipid liposome of this invention can be produced by the methods of any of these disclosures, the contents of which are incorporated herein by reference.

Various methodologies, such as sonication, homogenization, French Press application and milling can be used to prepare liposomes of a smaller size from larger liposomes. Extrusion (see U.S. Pat. No. 5,008,050) can be used to size reduce liposomes, that is to produce liposomes having a predetermined mean size by forcing the liposomes, under pressure, through filter pores of a defined, selected size. Tangential flow filtration (see WO89/008846), can also be used to regularize the size of liposomes, that is, to produce liposomes having a population of liposomes having less size heterogeneity, and a more homogeneous, defined size distribution. The contents of these documents are incorporated herein by reference. Liposome sizes can also be determined by a number of techniques, such as quasi-electric light scattering, and with equipment, e.g., Nicomp® particle sizers, well within the possession of ordinarily skilled artisans.

The liposomes of this invention can be unilamellar or multilamellar. Preferably the liposomes are unilamellar and have diameters of less than about 200 nm, more preferably, from greater than about 50 nm to less than about 200 nm. Smaller liposomes are generally believed to circulate longer in mammals, which are more quickly recognized by the mammals' reticuloendothelial systems ("RES"). Thus, 200 nm liposomes, for example, are generally expected to remain in circulation longer than liposomes having a 500-nm diameter. Longer circulation can enhance therapeutic efficacy by allowing more liposomes to reach their intended site of actions, e.g., tumors or inflammations. However, small liposomes, i.e., those generally less than 50 nm in diameter, carry amounts of bioactive agents which may be, in some cases, too low to be of sufficient therapeutic benefit.

$R_1$ of the ether lipid, the acyl chain attached at the carbon #1 position of its glycerol backbone by way of an oxygen, has the formula $Y_1Y_2$, wherein $Y_2$ is $CH_3$ or $CO_2H$ and $Y_1$ is $(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}$. n1 is equal to zero or is an integer of from 3 to 23; n3 is equal to zero or is an integer of from 1 to 21; n5 is equal to zero or is an integer of from 1 to 18; n7 is equal to zero or is an integer of from 1 to 15; n9 is equal to zero or is an integer of from 1 to 12; and each of n2, n4, n6 and 8 is independently equal to zero or 1. The sum of n1+2n2+n3+2n4+n5+2n6+n7+2n8+n9 is an integer of from 3 to 23. The hydrocarbon can have a terminal $CH_3$ or $CO_2H$ group; preferably, the terminal group is a methyl group. The hydrocarbon is preferably saturated, that is, it preferably has no double bonds between adjacent carbon atoms, each of n2, n4, n6 and n8 then being equal to zero. Accordingly, $R_1$ is preferably $(CH_2)_{n1}CH_3$. More preferably, $R_1$ is $(CH_2)_{17}CH_3$.

Alternatively, the hydrocarbon can have one or more double bonds, that is, it can be unsaturated, and one or more of n2, n4, n6 and n8 can be equal to 1. For example, when the unsaturated hydrocarbon has one double bond, n2 is equal to 1, n4, n6 and n8 are each equal to zero and $Y_1$ is $(CH_2)_{n1}CH=CH(CH_2)_{n3}$. n1 is then equal to zero or is an integer of from 1 to 21, and n3 is also zero or is an integer of from 1 to 21, at least one of n1 or n3 not being equal to zero.

Z is oxygen, sulfur, NH, or —NHC(O)—. Z then being connected to the methyl group by way of either the nitrogen or carbonyl carbon. Z can also be —OC(O)—, it then being connected to the methyl group by way of either the oxygen or carbonyl carbon atom. Preferably, Z is O; accordingly, this invention's glycerol-based ether lipids preferably have a methoxy group at the sn-2 position of their glycerol backbone.

$R_2$ is an alkyl group, or a halogen-substituted alkyl group, having the formula $(C(X_1)_{n10}(X_2)_{n11})_{n12}CX_3X_4X_5$, wherein each of $X_1$, $X_2$, $X_3$, $X_4$, and $X_5$ is independently hydrogen or a halogen, but is preferably hydrogen. n10 is equal to zero, 1 or 2; n11 is equal to zero, 1, or 2; and n12 is equal to zero or an integer of from 1 to 23, but is most preferably, zero, $R_2$ then being $CX_3X_4X_5$. $X_3$, $X_4$, and $X_5$ are most preferably H, and $R_2$ then being $CH_3$. Accordingly, the ether lipid preferably has a methyl group attached to its carbon #2. However, $R_2$ can then also be $CH_2F$, $CHF_2$ or $CF_3$. When n12 is not zero, the sum of n10+n11 is equal to 2, n12 is preferably equal to 1, and $R_2$ is preferably $CH_2CH_3$, $CH_2CF_3$ or $CF_2CF_3$.

Preferably, the ether lipid is one in which $Y_2$ is $CH_3$, $R_1$ is $(CH_2)_{n1}CH_3$, R2 is $CH_3$ and Z is O. The preferred ether lipid is therefore:

that is, 1-O-octadecyl-2-O-methyl-sn-glycero-3-phosphocholine ("ET-18-OCH₃" or "edelfosine").

"Underivatized phosphatidylethanolamines" included in the liposomes of this invention are phosphatidylethanolamines ("PE's") whose headgroups have not been derivatized by attachment thereto of chemical moieties. Underivatized PE's comprise one or two acyl chains, saturated or unsaturated and generally between 4 and 24 carbon atoms in length, and a phosphorylethanolamine group, i.e., $HO-CH_2-CH_2-NH_2$. Preferably, the underivatized PE is partially or wholly unsaturated, that is, it preferably has one or two acyl chains each having at least one double bond between adjacent carbon atoms in the chain. More preferably, presently, the PE is dioleoyl phosphatidylethanolamine ("DOPE").

"Sterols" generally affect the fluidity of lipid bilayers (see, for example, Lewis and McElhaney (1992) and Darnell et al. (1986)) Accordingly, sterol interactions with surrounding hydrocarbon chains generally inhibit emigration of these chains from the bilayer. The sterol component of the bilayers of the liposomes of this invention is preferably, but not necessarily, cholesterol, and can also be a variety of other sterolic compounds.

A "headgroup-derivatized" lipid is a lipid which, when present in a liposomal lipid bilayer with an ether lipid, can buffer the toxicity of the ether lipid. That is, the derivatized lipid can decrease the ether lipid's toxicity, such that it is generally less toxic than the free form of the ether lipid. Headgroup-derivatized lipids generally are amphipathic lipids comprising one or more hydrophobic acyl chains, and a phosphorylethanolamine group to which a suitable chemical moiety has been attached. The acyl chains typically contain from 4 to 24 carbon atoms, can be saturated or unsaturated and include palmitate and oleate chains, amongst others.

Preferred acyl chains are those which can adopt compatible packing configurations with the hydrophobic portions of other lipids present in the bilayer, and which can interact with an ether lipid such that release of the ether lipid from the bilayer is inhibited and ether lipid toxicity is buffered. More preferably, the headgroup derivatized lipid used herein is dipalmitoyl phosphatidylethanolamine ("DPPE"), palmitoyloleoyl phosphatidylethanolamine ("POPE") or dioleoyl phosphatidylethanolamine ("DOPE"). Most preferably, presently, the lipid is DOPE.

Chemical moieties suitable for attachment to such lipids are those, such as dicarboxylic acids, gangliosides, polyethylene glycols, polyalkyl ethers and the like, which can be attached to a phosphorylethanolamine and which give rise to lipids having toxicity buffering, circulation-enhancing properties. Means of identifying chemical moieties suitable, for example by subjecting derivatized lipids to in vitro and in vivo toxicity testing, are well known to, and readily practiced by, ordinarily skilled artisans given the teachings of this invention. Means of attaching chemical moieties to polar groups are also well known to, and readily practiced by, ordinarily skilled artisans.

Toxicity buffering capacities of headgroup-derivatized lipids can be determined by a number of in vitro and in vivo testing methods well known to, and readily practiced by, ordinarily skilled artisans, given the teachings of this invention. For example, ether lipid-induced red blood cell (RBC) hemolysis can be examined in vitro by combining an ether lipid with an RBC suspension, incubating the combination, and then quantitating the percentage of RBC lysis by spectrophotometry.

Therapeutic window "TW" is derived from the relationship between induction of hemolysis and growth inhibition of tumor cells and can be determined in accordance with the formula $Hl_{50}/Gl_{50}$ ("$Gl_{50}$" equals the dose of an agent inducing fifty percent growth inhibition in a population of cells exposed to the agent). Larger TW values indicate increased hemolytic induction relative to growth inhibition, and thus, relatively less therapeutic benefit than when an agent has a higher TW.

Generally, when a bioactive agent's TW is less than 1, the agent cannot be administered to achieve 50% growth inhibition without causing generally unacceptable levels of hemolysis. When the TW is about 1 or greater, the bioactive agent can be administered without inducing generally unacceptable levels of hemolysis. Typically, the higher the TW value, the more therapeutically effective is the agent tested. Ether lipid liposomes having bilayers comprising headgroup-derivatized lipids can have TWs of greater than 1. Preferably, the TW of an ether lipid in a liposomal bilayer also comprising a headgroup-derivatized lipid is greater than about 1.5, more preferably, greater than about 2 and still more preferably, greater than about 3.

Headgroup-derivatized lipids can also be circulation-enhancing lipids, that is, the modifications directed to lipid toxicity buffering can also afford circulation enhancement. Accordingly, headgroup-derivatized lipids can inhibit clearance of liposomes from the circulatory systems of animals to which they have been administered. Liposomes are generally believed to be cleared from an animal's body by way of its reticuloendothelial system (RES). Avoiding RES clearance means that the frequency of liposome administration can be reduced, and that less of a liposome-associated bioactive agent need be administered to achieve desired serum levels of the agent. Enhanced circulation times can also allow targeting of liposomes to non-RES containing tissues.

Liposome outer surfaces are believed to become coated with serum proteins, such as opsonins, in animals' circulatory systems. Without intending in any way to be limited by theory, it is believed that liposome clearance can be inhibited by modifying the outer surface of liposomes such that binding of serum proteins thereto is generally inhibited. Effective surface modification, that is, alterations to the outer surfaces of liposomes which result in inhibition of opsonization and RES uptake, is believed to be accomplished by incorporating into liposomal bilayers lipids whose polar headgroups have been derivatized by attachment thereto of a chemical moiety which can inhibit the binding of serum proteins to liposomes such that the pharmacokinetic behavior of the liposomes in the circulatory systems of animals is altered (see, e.g., Blume et al. (1993); Gabizon et al. (1993); Park et al. (1992); Woodle et al. U.S. Pat. No. 5,013,556; and, U.S. Pat. No. 4,837,028).

Presently, dicarboxylic acids, such as glutaric, sebacic, succinic and tartaric acids, are preferred components of headgroup-derivatized lipids. Most preferably, the dicarboxylic acid is glutaric acid ("GA"). Accordingly, suitable headgroup-derivatized lipids include phosphatidylethanolamine-dicarboxylic acids such as dipalmitoyl phosphatidylethanolamine-glutaric acid ("DPPE-GA"), palmitoyloleoyl phosphatidylethanolamine-glutaric acid ("POPE-GA") and dioleoyl phosphatidylethanolamine-glutaric acid ("DOPE-GA"). Most preferably, the derivatized lipid is DOPE-GA. The headgroup-derivatized can comprise from about 5 mole percent to about 50 mole percent of the liposome's lipid bilayer, but most preferably comprises about 10 mole percent of the bilayer.

The liposomes of this invention can comprise one or more additional lipids, that is, lipids in addition to the sterol, underivatized PE, headgroup-derivatized lipid and ether lipid already present in the liposomes' bilayers. Additional lipids are selected for their ability to adapt compatible packing conformations with the other lipid components of the bilayer such that the lipid constituents are tightly packed and release of the lipids from the bilayer is inhibited. Lipid-based factors contributing to compatible packing conformations are well known to ordinarily skilled artisans and include, without limitation, acyl chain length and degree of unsaturation, as well as the headgroup size and charge. Accordingly, suitable additional lipids, including various phosphatidylcholines ("PC's") such as egg phosphatidylcholine ("EPC") or dioleoyl phosphatidylcholine ("DOPC") can be selected by ordinarily skilled artisans without undue experimentation.

Preferred embodiments of this invention have the underivatized PE being DOPE, the sterol being cholesterol ("chol"), the ether lipid being ET-18-OCH$_3$ and the headgroup-derivatized lipid being DOPE-GA. Most preferably, presently, the liposome comprises DOPE, chol, ET-18-O-CH$_3$ in a respective molar ratio of 4:3:1:2, wherein DOPE comprises 40 mole % of the liposomes' bilayers, chol 30% mole, DOPE-GA 10 mole % and the ether lipid 20 mole %. Preferably, the liposomes are unilamellar and have an average diameter of from about 50 nm to about 200 nm, "average" meaning that the median diameter of a population of this invention's liposomes is between 50 and 200 nm.

The liposome can comprise an additional bioactive agent, that is, a bioactive agent in addition to the ether lipid. A "bioactive agent" is any compound or composition of matter that can be administered to animals, preferably humans. Such agents can have biological activity in animals; the agents can also be used diagnostically in the animals.

Bioactive agents which may be associated with liposomes include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid, and purine and pyrimidine analogs; antineoplastic agents such as the anthracycline antibiotics and plant alkaloids; sterols such as cholesterol; carbohydrates, e.g., sugars and starches; amino acids, peptides, proteins such as cell receptor proteins, immunoglobulins, enzymes, hormones, neurotransmitters and glycoproteins; dyes; radiolabels such as radioisotopes and radioisotope-labelled compounds; radiopaque compounds; fluorescent compounds; mydriatic compounds; bronchodilators; local anesthetics; and the like.

Liposomal bioactive agent formulations can enhance the therapeutic index of the bioactive agent, for example by buffering the agent's toxicity. Liposomes can also reduce the rate at which a bioactive agent is cleared from the circulation of animals. Accordingly, liposomal formulation of bioactive agents can mean that less of the agent need be administered to achieve the desired effect. Additional bioactive agents preferred for the liposome of this invention include antimicrobial, anti-inflammatory and antineoplastic agents, or therapeutic lipids, for example, ceramides. Most preferably, the additional bioactive agent is an antineoplastic agent.

Liposomes can be loaded with one or more biologically active agents by solubilizing the agent in the lipid or aqueous phase used to prepare the liposomes. Alternatively, ionizable bioactive agents can be loaded into liposomes by first forming the liposomes, establishing an electrochemical potential, e.g., by way of a pH gradient, across the outermost liposomal bilayer, and then adding the ionizable agent to the aqueous medium external to the liposome (see Bally et al. U.S. Pat. No. 5,077,056 and WO86/01102).

The liposome of this invention can be dehydrated, stored and then reconstituted such that a substantial portion of its internal contents are retained. Liposomal dehydration generally requires use of a hydrophilic drying protectant such as a disaccharide sugar at both the inside and outside surfaces of the liposome bilayers (see U.S. Pat. No. 4,880,635). This hydrophilic compound is generally believed to prevent the rearrangement of the lipids in the liposome, so that the size and contents are maintained during the drying procedure and through subsequent rehydration. Appropriate qualities for such drying protectants are that they be strong hydrogen bond acceptors, and possess stereochemical features that preserve the intramolecular spacing of the liposome bilayer components. Alternatively, the drying protectant can be omitted if the liposome preparation is not frozen prior to dehydration, and sufficient water remains in the preparation subsequent to dehydration.

Also provided herein is a pharmaceutical composition comprising a pharmaceutically acceptable carrier and the liposome of this invention. "Pharmaceutically acceptable carriers" as used herein are those media generally acceptable for use in connection with the administration of lipids and liposomes, including liposomal bioactive agent formulations, to animals, including humans. Pharmaceutically acceptable carriers are generally formulated according to a number of factors well within the purview of the ordinarily skilled artisan to determine and account for, including without limitation: the particular liposomal bioactive agent used, its concentration, stability and intended bioavailability; the disease, disorder or condition being treated with the liposomal composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, Nairn (1985)). Typical pharmaceutically acceptable carriers used in parenteral bioactive agent administration include, for example, D5W, an aqueous solution containing 5% weight by volume of dextrose, and physiological saline. Pharmaceutically acceptable carriers can contain additional ingredients, for example those which enhance the stability of the active ingredients included, such as preservatives and anti-oxidants.

Further provided is a method of treating a mammal afflicted with a cancer, e.g., a brain, breast, lung, colon or ovarian cancer, or a leukemia, lymphoma, sarcoma, carcinoma, which comprises administering the pharmaceutical composition of this invention to the mammal, ether lipids being believed to be selectively cytotoxic to tumor cells. Generally, liposomal ether lipids can be used to treat cancers treated with free, that is, nonliposomal, ether lipids. However, encapsulation of an ether lipid in a liposome can enhance its therapeutic index, and therefore make the liposomal ether lipid a more effective treatment.

An amount of the composition comprising an anticancer effective amount of the ether lipid, typically from about 0.1 to about 1000 mg of the lipid per kg of the mammal's body, is administered, preferably intravenously. For the purposes of this invention, "anticancer effective amounts" of liposomal ether lipids are amounts effective to inhibit, ameliorate, lessen or prevent establishment, growth, metastasis or invasion of one or more cancers in animals to which the ether lipids have been administered. Anticancer effective amounts are generally chosen in accordance with a number of factors, e.g., the age, size and general condition of the subject, the cancer being treated and the intended route of administration, and determined by a variety of means, for example, dose ranging trials, well known to, and readily practiced by, ordinarily skilled artisans given the teachings of this invention. Antineoplastic effective amounts of the liposomal ether lipid of this invention are about the same as such amounts of free, nonliposomal, ether lipids.

Preferably, the liposome administered is a unilamellar liposome having an average diameter of from about 50 nm to about 200 nm. The anti-cancer treatment method can include administration of one or more bioactive agents in addition to the liposomal ether lipid, these additional agents preferably, but not necessarily, being included in the same liposome as the ether lipid. The additional bioactive agents, which can be entrapped in liposomes' internal compartments or sequestered in their lipid bilayers, are preferably, but not necessarily, anticancer agents or cellular growth promoting factors.

This invention also provides a method of treating a mammal afflicted with an anti-inflammatory disorder, e.g., arthritic conditions, asthmatic disorders and allergic reactions, comprising administering to the mammal an amount of the pharmaceutical composition provided herein sufficient to contain an anti-inflammation effective amount of the liposomal ether lipid. Inflammation is a process of cytological and histological reactions occurring in affected blood vessels, and surrounding tissues, in response to an injury (see, e.g., Stedman's Medical Dictionary (Illustrated) (1982)). Inflammatory responses to such stimuli include local reactions and resulting morphological changes, destruction or removal of injurious materials and activation of repair mechanisms. Thus, inflammation can be part of the process by which animals heal themselves.

However, inflammation can also occur in response to abnormal physiological stimuli, and can cause problems in the body. Joints, for example, become inflamed in arthritic conditions such as gout, filary arthritis, rheumatoid arthritis and Lyme disease (see, e.g., Stedman's Medical Dictionary (Illustrated), supra at pages 123–124). These states may be characterized by the extravasation of cells, i.e. the egress of cells from the circulation into the inflamed area. Agents which can inhibit such extravasation, or which can otherwise inhibit inflammatory responses to abnormal physiological stimuli, can be used to ameliorate the inflammation. An "anti-inflammation effective amount" of a liposomal ether lipid, typically from about 0.1 mg to about 1000 mg per kg of a treated mammal's body weight, is any amount of the ether lipid effective to ameliorate, inhibit or prevent inflammatory responses or reactions in animals afflicted with conditions characterized by abnormal inflammation, i.e., inflammation which is in response to abnormal physiological stimuli and which is not part of the body's normal repair processes in response to an injury.

This invention will be better understood from the following examples. However, those of ordinary skill in the art will readily understand that these examples are merely illustrative of the invention as defined in the claims which follow thereafter.

EXAMPLES

Example 1

Preparation

Liposomes were prepared with edelfosine (ET-18-O-$CH_3$, 5 mg/ml), various other lipids obtained from Avanti Polar Lipids, Birmingham, Ala., and cholesterol (Sigma Chemical Co.). Briefly, the lipids were dissolved in an organic solvent, such as chloroform, at various mole ratios. The organic solvent was then removed, and the dried lipids were rehydrated, e.g., with Dulbecco's phosphate-buffered saline (D-PBS) (Gibco BRL Life Technologies, Grand Island, N.Y.). The resulting liposomes were extruded through 0.1 micron Nuclepore® filters (see, for example, Mayer et al., 1985). Liposome sizes were then determined by light scattering, using a Nicomp® Model 370 Submicron Particle Sizer.

Example 2
Red Blood Cell ("RBC") Hemolysis Assay

A 4% suspension of red blood cells (RBCs), 0.5 ml, was washed three times in PBS and then incubated with free (non-liposomal) ether lipid or liposomal ether lipid, prepared as described above. These samples were vortexed on a 37 deg. C. agitator for 20 hours, and were then centrifuged for 10 minutes at 3000 rpm. 0.2 ml of the resulting supernatant was diluted to 1 ml with water, and the percentage hemolysis in the sample was quantitated by spectrophotometric examination at 550 nm.

Results from these studies are presented in Table 1 (see below), wherein the concentration (μM) of edelfosine required to cause 10% RBC hemolysis ("$Hl_{10}$") in each formulation is set forth. The table's first column is a shorthand designation of the particular formulation, "ELL" standing for "ether lipid liposome." The second column indicates the components of the formulation tested, including dioleoyl phosphatidylethanolamine "(DOPE"), cholesterol ("CHOL"), dioleoyl-phosphatidylethanolamine-glutaric acid ("DOPE-GA"), dioeloyl phosphatidylcholine ("DOPC"), palmitoyloleoyl phosphatidylcholine ("POPC"), distearoyl phosphatidylcholine ("DSPC"), egg phosphatidylcholine ("EPC") and edelfosine ("EL," for ether lipid). The respective molar ratios of the various lipid components are also set forth. The last row of the table gives the $Hl_{10}$ value for edelfosine alone, i.e., not incorporated in a liposome.

TABLE 1

| Formulation | Composition | $Hl_{10}$ |
|---|---|---|
| ELL 20 | DOPE:CHOL:DOPE—GA:EL<br>4    3    1    2 | 1726 ± 160 |
| ELL 12 | DOPC:CHOL:DOPE—GA:EL<br>4    3    1    2 | 670 ± 60 |
| ELL 40 | POPC:CHOL:DOPE—GA:EL<br>4    3    1    2 | 65 ± 6 |
| ELL 28 | DSPC:CHOL:DOPE—GA:EL<br>4    3    1    2 | 32 ± 3 |
| ELL 25 | DOPE:CHOL:DOPE—GA:EL<br>3    3    1    3 | 537 ± 50 |
| ELL 30 | EPC:CHOL:DOPE—GA:EL<br>4    3    1    2 | 314 ± 30 |
| Edelfosine | — | 5 ± 1 |

Example 3
Fluorescence Spectroscopy

Figure 1:
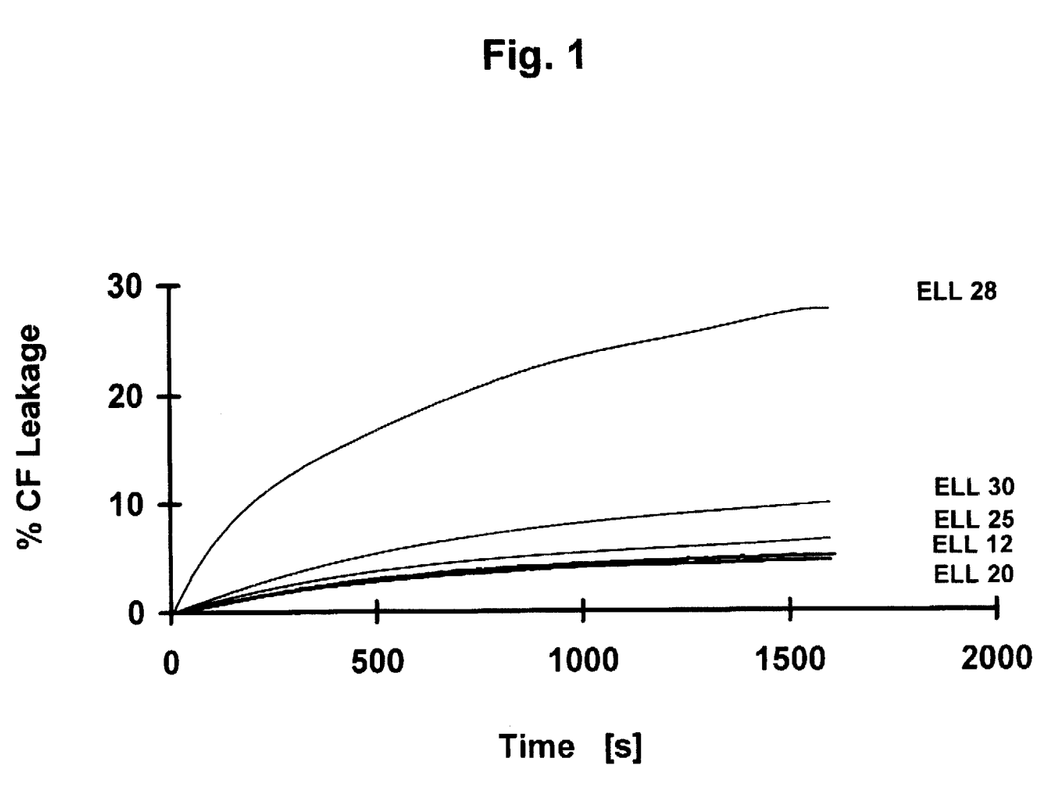
FIG. 1. Time Course of Carboxyfluorescein Leakage from Liposomal Edelfosine Formulations Incubated at 48 deg. Celsius in PBS. ELL 28 (uppermost curve, "ELL" indicating "ether lipid liposome"): Distearoyl phosphatidylcholine ("DSPC"); cholesterol ("CHOL"); dioleoyl phosphatidylethanolamine-glutaric acid ("DOPE-GA"); edelfosine "EL," standing for "ether lipid" (the respective molar ratio of these lipid components being 4:3:1:2); ELL 30 (second from top curve): EPC:CHOL:DOPE-GA:EL (4:3:1:2); ELL 25 (middle curve): DOPE:CHOL:DOPE-GA:EL (3:3:1:3); ELL 12 (second from bottom curve): DOPC:CHOL:DOPE-GA:EL (4:3:1:2); and, ELL 20 (bottom curve): DOPE:CHOL:DOPE-GA:EL (4:3:1:2). Y-axis: % CF Leakage; x-axis: time (seconds).

Liposomes were prepared as described above, and in the presence of an aqueous solution of 0.1M 6-carboxyfluorescein ("CF"); free CF was then removed by gel filtration. CF efflux from liposomes over time was monitored by measuring, at 520 nm (excitation at 490 nm), increases in CF fluorescence in the aqueous phase external to the liposomes, upon their incubation in PBS at 48 deg. C. Fluorescence values, presented in FIG. 1 herein, are expressed as a percentage increase in CF fluorescence relative to the total CF fluorescence found after disrupting liposomes with Triton X-100.

Figure 2:
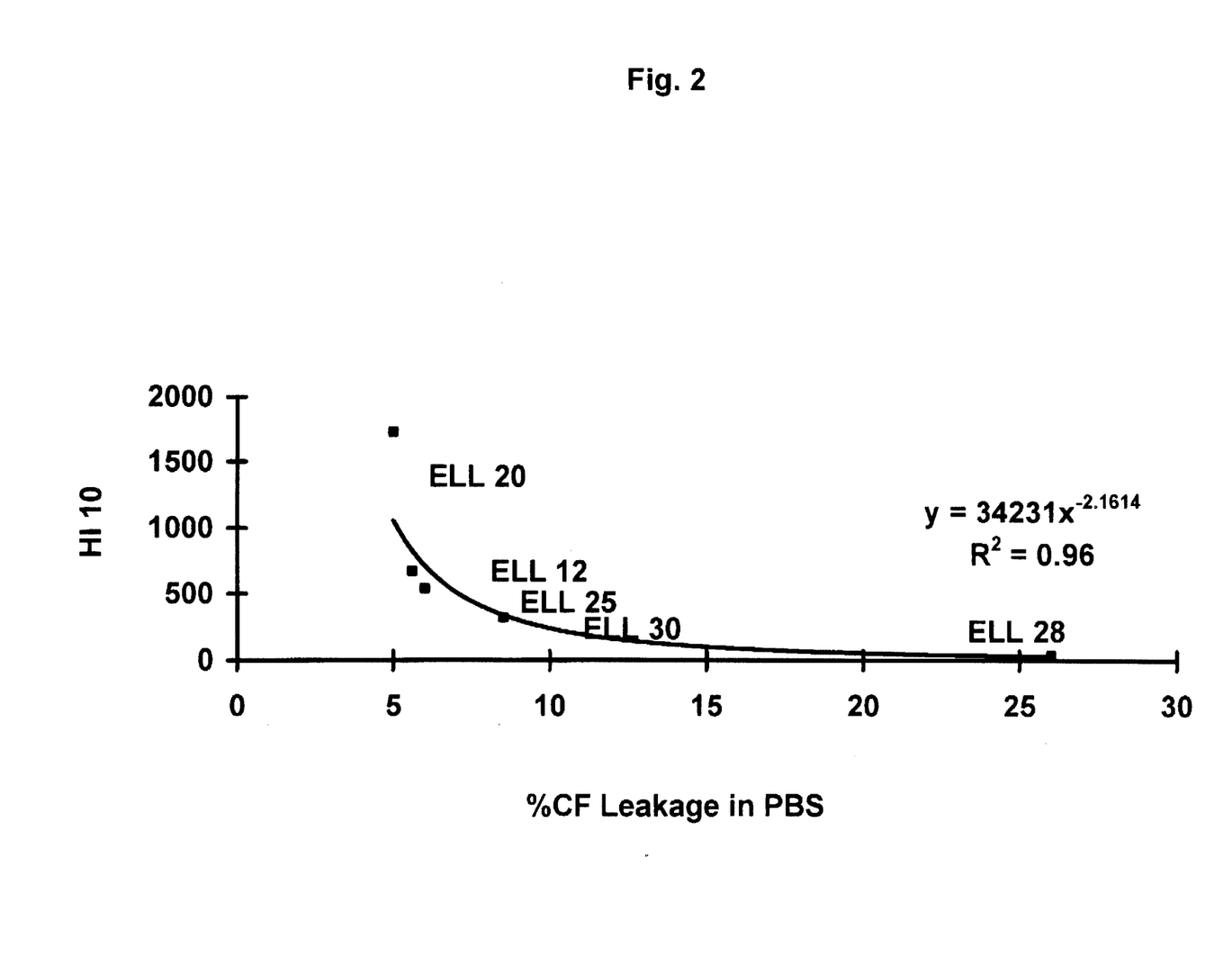
FIG. 2. Comparison of Hemolytic Activity and CF Leakage in Ether Lipid Liposomes. From top-to-bottom: ELL 20 - ELL 12 - ELL 25 - ELL 30 - ELL 28 ($y=34231x^{-2.1614}$; $R^2=0.96$). Y-axis: $Hl_{10}$; x-axis: % CF leakage upon incubation in PBS.
Figure 3:
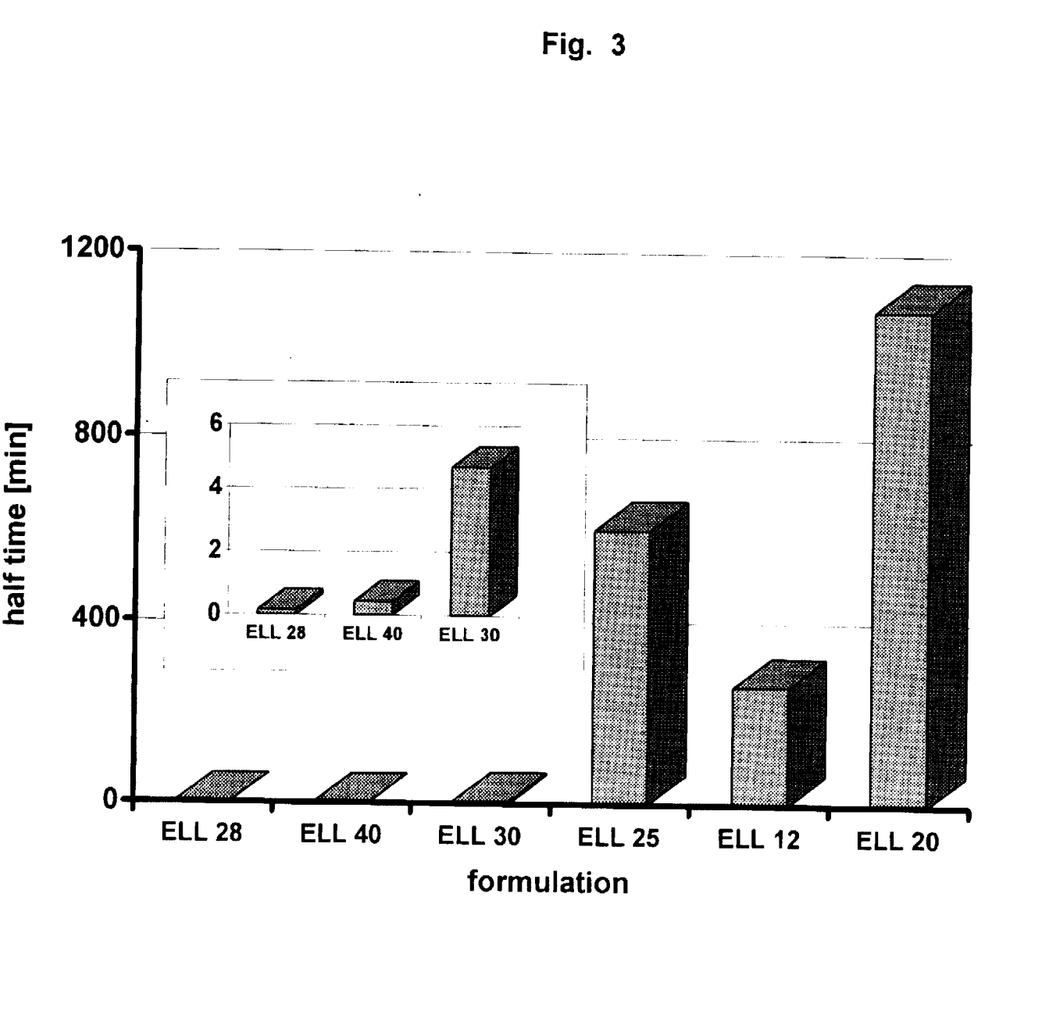
FIG. 3. Stability of Ether Lipid Liposomal Formulations on Incubation in 0.5% Serum at 37 Degrees Celsius. Y-axis: time (minutes); x-axis (from left-to-right): ELL 28, ELL 40, ELL 30; ELL 25; ELL 12; ELL 20. Inset: Y-axis: time (minutes); x-axis: ELL 28, ELL 40, ELL 30.

FIG. 2 herein compares hemolytic activity and CF leakage in various liposomal formulations described in Table 1, upon incubation of the liposomes in PBS at 48 deg. C. for 25 minutes. FIG. 3 compares the time required for 50% CF leakage in various liposomal formulations, upon their incubation in 0.5% serum at 37 deg. C.

References Cited
U.S. Patent Documents
U.S. Pat. Nos. 4,159,988, 4,163,748, 4,235,871, 4,382,035, 4,522,803, 4,588,578, 4,734,225, 4,804,789, 4,837,028, 4,920,016, 4,975,282, 5,008,050, 5,013,556, 5,030,453, 5,059,421, 5,077,056, 5,169,637, 3,752,886

Foreign Patent Documents
WO89/008846, 1,583,661, 4,132,345

Others
Bazill and Dexter, Cancer Res. 50: 7505 (1990).
Berdel, Br. J. Cancer 64: 208 (1991); Berdel, Onkologie 13: 245 (1990).
Bhatia and Hadju, Lipids 26(12): 1424 (1991).
Blume et al., Biochim. Biophys. Acta. U1149U: 180 (1993)
Darnell et al., *Molecular Cell Biology*, Scientific American Books, Inc. (1986), New York, pp. 573–575.
Deamer and Uster, "Liposome Preparation: Methods and Mechanisms," in: *Liposomes* (M. Ostro, ed.), Marcel Dekker, Inc., New York (1983), pp. 27–52.
Dietzfelbinger et al., Cancer Res. 53: 3747 91993).
Gabizon et al., Pharm. Res. 10(5): 703 91993)
Layton et al., Eur. J. Cancer 16: 64 (1980).
Lewis and McElhaney, "The Mesomorphic Phase Behavior of Lipid Bilayers," in *The Structure of Biological Membranes* (P. Yeagle, ed.), CRC Press, Inc. (1992), Boca Raton, Fla., pp. 73–155, at pp. 123–126.
Mayer et al., Biochim. Biophys. Acta 817: 193 (1985).
Muschiol et al., Lipids 22(11): 930 (1987).
Nairn, in: *Remington's Pharmaceutical Science* (A. Gennaro, ed.), Mack Publishing Co., Easton, Pa., (1985), pp. 1492–1517.
Paphadjopoulos et al., Biochem. Biophys. Acta 135: 624 (1968).
Park et al., Biochim. Biophys. Acta. 1108: 257 (1992).
Powis et al., Cancer Res. 52: 2835 (1992).
Powis et al., Cancer Res. 50: 2203 (1990).
Reed et al., Life Sci. 49: 1221 (1991).
Runge et al., JNCI. 64(6): 1301 (1980).
*Stedman's Medical Dictionary (Illustrated)* (24th edition, J. V. Basmajian et al., eds.), Williams and Wilkins, Baltimore, Md. (1982), pp. 707–708.
Tritton and Hickman, Cancer Cells 2(4): 95 (1990).
Workman, Cancer Cells 3(8): 315 (1991).
Workman et al., Biochem. Pharmacol. 41(2): 319 (1991).
Zeisig et al., Anti-Cancer Drugs 4: 57 (1993).

What is claimed is:

1. A liposome having a lipid bilayer which comprises:
   (a) an underivatized phosphatidylcholine;
   (b) a sterol;
   (c) a lipid which is a phosphatidylethanolamine linked to a dicarboxylic acid at the ethanolamine group of the phosphatidylethanolamine: and,
   (d) an ether lipid having the formula:

wherein $R_1$ is $Y_1Y_2$ $Y_2$ is $CH_3$ or $CO_2H$, $Y_1$ is $(CH_2)_{n1}$ $(CH=CH)_{n2}(CH_2)_{n3}(CH=CH)_{n4}(CH_2)_{n5}(CH=CH)_{n6}$ $(CH_2)_{n7}$ $(CH=CH)_{n8}(CH_2)_{n9}$, the sum of n1+2n2+n3+2n4+n5+2n6+n7+2n8+n9 is an integer of from 2 to 22, n1 is zero or an integer of from 1 to 22, n3 is zero or an integer of from 1 to 19, n5 is zero or an integer of from 1 to 16, n7 is zero or an integer of from zero to 13, n9 is zero or an integer of from 1 to 10, and each of n2, n4, n6 and 8 is independently zero or 1;
wherein Z is oxygen or sulfur and $R_2$ is $CH_3$;
wherein $R_3$ is $O-P(O)_2-O-CH_2CH_2N(CH_3)_3$;
and wherein the phosphatidylethanolamine-dicarboxylic acid comprises from about 5 mole percent to about 20 mole percent of the lipid bilayer and the ether lipid comprises from greater than about 10 mole percent to less than about 30 mole percent of the lipid bilayer.

2. The liposome of claim 1 which is a unilamellar liposome having a diameter of from greater than about 50 nm to less than about 200 nm.

3. The liposome of claim 1, wherein the underivatized phosphatidylcholine is an unsaturated or partially unsaturated phosphatidylcholine.

4. The liposome of claim 3, wherein the underivatized phosphatidylcholine is dioleoyl phosphatidylcholine.

5. The liposome of claim 1, wherein the sterol is cholesterol.

6. The liposome of claim 1, wherein the phosphatidylethanolamine is selected from the group consisting of dipalmitoyl phosphatidylethanolamine, palmitoyloleoyl phosphatidylethanolamine and dioleoyl phosphatidylethanolamine.

7. The liposome of claim 6, wherein the phosphatidylethanolamine is dioleoyl phosphatidylethanolamine.

8. The liposome of claim 1, wherein the dicarboxylic acid is selected from the group consisting of glutaric acid, sebacic acid, succinic acid and tartaric acid.

9. The liposome of claim 8, wherein the dicarboxylic acid is glutaric acid.

10. The liposome of claim 1, wherein the phosphatidylethanolamine is dioleoyl phosphatidylethanolamine and the dicarboxylic acid is glutaric acid.

11. The liposome of claim 1, wherein $Y_2$ is $CH_3$, $R_1$ is $(CH_2)_{n1}CH_3$, Z is O and $R_2$ is $CH_3$.

12. The liposome of claim 11, wherein the ether lipid is

13. The liposome of claim 1, wherein the underivatized phosphatidylcholine is dioleoyl phosphatidylcholine, the sterol is cholesterol, the phosphatidylethanolamine is dioleoyl phosphatidylethanolamine, the dicarboxylic acid is glutaric acid and the ether lipid is 14. The liposome of claim 13, wherein the bilayer comprises about 20 mole percent of the ether lipid, about 10 mole percent of the phosphatidylethanolamine-dicarboxylic acid about 30 mole percent cholesterol and about 40 mole percent dioleoyl phosphatidylcholine.

15. The liposome of claim 1, comprising an additional bioactive agent.

16. A pharmaceutical composition comprising a pharmaceutically acceptable carrier and the liposome of claim 1.

17. A method of treating a mammal afflicted with a cancer which comprises administering to the mammal an amount of the pharmaceutical composition of claim 16 comprising from about 0.1 mg of the ether lipid per kg of the body weight of the mammal to about 1000 mg per kg, wherein the cancer is selected from the group consisting of lung cancers, brain cancers, colon cancers, ovarian cancers, breast cancers, leukemias, lymphomas, sarcomas and carcinomas.

18. The method of claim 17, comprising administering to the mammal an additional biologically active agent.

19. The method of claim 18, wherein the additional agent is selected from the group consisting of antineoplastic agents, antimicrobial agents, and hematopoietic cell growth stimulating agents.

20. The method of claim 17, wherein the liposome is a unilamellar liposome having a diameter of from about 50 nm to about 200 nm.

* * * * *